(12) United States Patent
Narahara et al.

(10) Patent No.: US 10,112,195 B2
(45) Date of Patent: Oct. 30, 2018

(54) FLOW CELL FOR NUCLEIC ACID ANALYSIS AND NUCLEIC ACID ANALYZER

(71) Applicant: HITACHI HIGH-TECHNOLOGIES CORPORATION, Tokyo (JP)

(72) Inventors: Masatoshi Narahara, Tokyo (JP); Tomohiro Shoji, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 91 days.

(21) Appl. No.: 14/907,844

(22) PCT Filed: Jun. 11, 2014

(86) PCT No.: PCT/JP2014/065405
§ 371 (c)(1),
(2) Date: Jan. 27, 2016

(87) PCT Pub. No.: WO2015/015913
PCT Pub. Date: Feb. 5, 2015

(65) Prior Publication Data
US 2016/0167049 A1    Jun. 16, 2016

(30) Foreign Application Priority Data
Jul. 31, 2013 (JP) ................ 2013-158426

(51) Int. Cl.
*B01L 3/00* (2006.01)
*C12Q 1/6869* (2018.01)

(52) U.S. Cl.
CPC ...... *B01L 3/502715* (2013.01); *C12Q 1/6869* (2013.01); *B01L 3/5025* (2013.01);
(Continued)

(58) Field of Classification Search
CPC ........ C12Q 2565/543; C12Q 2565/629; C12Q 1/6825; B01L 2300/0877; B01L 3/502715;
(Continued)

(56) References Cited

U.S. PATENT DOCUMENTS 7,897,737 B2   3/2011   Wu et al.
8,039,817 B2   10/2011  Feng et al.
(Continued)

FOREIGN PATENT DOCUMENTS

JP   2002-330799 A   11/2002
JP   2002-340901 A   11/2002
(Continued)

OTHER PUBLICATIONS

International Search Report of PCT/JP2014/065405.
(Continued)

*Primary Examiner* — Sally A Merkling
(74) *Attorney, Agent, or Firm* — Mattingly & Malur, PC

(57) ABSTRACT

Provided is a flow cell for nucleic acid analysis used for a sequence reaction with photocleavable nucleotides where an efficiency of the photocleaving reaction can be enhanced and noise upon florescence detection can be mitigated, thereby improving the accuracy of sequencing, shortening a runtime, and extending a read length. The flow cell for nucleic acid analysis includes a first substrate 101 provided with an optical filter 102 reflecting first light for changing a chemical structure of a substance in a flow passage, a hollow sheet 103 having a hollow portion for forming the flow passage, and a second substrate 105 transmitting the first light, in which the first substrate, the hollow sheet, and the second substrate are attached to each other.

12 Claims, 12 Drawing Sheets

A-A' CROSS-SECTION

(52) U.S. Cl.
CPC ... *B01L 2200/10* (2013.01); *B01L 2300/0654* (2013.01); *B01L 2300/0816* (2013.01); *B01L 2300/0877* (2013.01); *B01L 2300/0887* (2013.01); *B01L 2300/163* (2013.01); *B01L 2300/168* (2013.01)

(58) Field of Classification Search
CPC .......... B01L 2200/025; B01L 2300/168; B01J 2219/00637; G01N 2021/0346; G01N 21/05; G01N 21/6486
See application file for complete search history.

(56) References Cited

U.S. PATENT DOCUMENTS

| | | | |
|---|---|---|---|
| 8,241,573 B2 * | 8/2012 | Banerjee | G01N 21/6456 382/128 |
| 2009/0208194 A1 | 8/2009 | Honjo et al. | |
| 2012/0208194 A1 | 8/2012 | Liu et al. | |
| 2012/0316086 A1 * | 12/2012 | Lin | G01N 27/447 506/26 |
| 2013/0084629 A1 | 4/2013 | Nakazawa et al. | |
| 2015/0107993 A1 * | 4/2015 | Izquierdo | C12Q 1/02 204/403.01 |

FOREIGN PATENT DOCUMENTS

| | | |
|---|---|---|
| JP | 2006-214956 A | 8/2006 |
| JP | 2011-506265 A | 3/2011 |
| WO | 2004/018493 A1 | 3/2004 |
| WO | 2008/070749 A2 | 6/2008 |
| WO | 2011/142085 A1 | 11/2011 |

OTHER PUBLICATIONS

Marcel Margulies et al., "Genome sequencing in microfabricated high-density picolitre reactors", Nature, Sep. 15, 2005, pp. 376-380, vol. 437.

Jay Shendure et al., "Accurate Multiplex Polony Sequencing of an Evolved Bacterial Genome", Science, Sep. 9, 2005, pp. 1728-1732, vol. 309.

Timothy D. Harris et al., "Single-Molecule DNA Sequencing of a Viral Genome", Science, Apr. 4, 2008, pp. 106-109, vol. 320.

* cited by examiner

FLOW CELL FOR NUCLEIC ACID ANALYSIS AND NUCLEIC ACID ANALYZER

TECHNICAL FIELD

The present invention relates to a flow cell for nucleic acid analysis and a nucleic acid analyzer.

BACKGROUND ART

New techniques for determining base sequences of DNA or RNA have been implemented.

In a method using the conventional electrophoresis, a sample of DNA fragments for sequencing or cDNA fragments synthesized by reverse transcription from an RNA sample is prepared in advance and a dideoxy reaction is carried out by performing the known Sanger sequencing technology. Thereafter, electrophoresis is performed and a molecular weight separation and development pattern is measured for analysis.

Contrary to this, recently, a method has been proposed whereby sequence information of a number of fragments is determined in parallel by fixing a number of sample DNA fragments to a substrate.

In NPL 1, a microparticle is used as a carrier for carrying DNA fragments and PCR is performed on the microparticle. Thereafter, the microparticles supporting the DNA fragments, having been amplified by PCR, are added to a plate provided with a number of holes having a hole diameter matched with the size of the microparticle, thereby reading the DNA fragments by the pyrosequencing method.

Also in NPL 2, a microparticle is used as a carrier for carrying DNA fragments and PCR is performed on the microparticle. Thereafter, the microparticles are spread over a glass substrate and fixed thereto. An enzyme reaction (ligation) is carried out on the glass substrate and a primer attached with a florescent dye is allowed to be incorporated, whereby performing florescence detection allows for obtaining sequence information on each of the fragments.

Furthermore in NPL 3, a number of DNA probes having the same sequence are fixed to a substrate. Also, after cleaving a DNA sample, an adapter sequence of a complementary chain to a sequence of the DNA probe is added to a terminal of each of the sample DNA fragments. Subjecting the above to hybridization on the substrate allows for fixing the sample DNA fragments molecule by molecule to the substrate in a random manner. In this case, a DNA elongation reaction is carried out on the substrate and a substrate attached with a florescent dye is allowed to be incorporated. Thereafter, washing off unreacted substrates or florescence detection is performed and sequence information of the sample DNA is obtained.

In this manner, a method has been developed and implemented whereby sequence information of a number of fragments is determined in parallel by fixing a number of sample nucleic acid fragments to a substrate.

PTL 1 discloses details of a method for determining a number of pieces of sequence information in parallel. A sequence reaction is carried out in a flow cell having a flow passage therein. A surface of the flow passage is coated with acrylamide and a forward primer and a reverse primer are grafted on the acrylamide. A solution containing target templates of a plurality of types is introduced into the flow cell and then an amplification reaction is carried out on a substrate by subjecting the flow cell to temperature cycling, thereby forming, on the substrate, a plurality of colonies having the same sequence as the template. One colony is a collection of a plurality of copy templates having been amplified while the copy template has the same sequence as or a complementary sequence to the target template. After amplification, a sequencing primer is hybridized with the template in the colony, thereby allowing the sequence reaction to be carried out. For the sequence reaction, a nucleotide disclosed in WO 2004/018493 is used. The nucleotide has a florescent molecule via a cleavable linker and a leaving group at 3'-oxygen of its sugar. In the sequence reaction, four types of nucleotides derived from four types of bases A, T, C, and G are used. Each of the four types of nucleotides is labeled with a florescent dye different from each another. A solution containing a polymerase and the four types of nucleotides is injected into the flow cell to allow the sequence primer to incorporate the nucleotides. Thereafter, the sequence primer incorporated with the florescence is subjected to florescence detection. Here, since the nucleotides are incorporated in such a manner as to form a complementary sequence to the template sequence, detecting florescence of the nucleotides having been incorporated allows for determining a base sequence of the target template. After the florescence detection, the intramolecular linker is chemically cleaved to remove the florescent molecule. By repeating a cycle of incorporation of the nucleotides, florescence detection, removal of the florescent molecule, the base sequence of the template is determined.

CITATION LIST

Patent Literatures

PTL 1: US 2012/208194 A
PTL 2: WO 2004/018493
PTL 3: U.S. Pat. No. 7,897,737
PTL 4: U.S. Pat. No. 8,039,817
PTL 5: US 2009/208194 A

Non-Patent Literatures

NPL 1: Nature 2005, vol. 437, pp. 376-380.
NPL 2: Science 2005, vol. 309, pp. 1728-1732
NPL 3: Science 2008, vol. 320, pp. 106-109.

SUMMARY OF INVENTION

Technical Problem

Methods described in PTL 1 or PTL 2 have a problem of a low accuracy in sequencing due to incorporation of false nucleotides irrelevant to a base sequence of a template at a certain ratio. Also, as a base length of the template extends, a ratio, of templates incorporating false nucleotides in one colony, increases, thereby reducing true florescent signals. This results in a problem that the read length cannot be extended. Generally, in a process of sequencing, a base sequence of a fragmented template is determined and thereafter pieces of the sequences are aligned on a computer. When a read length is short, however, there are problems such as lower alignment accuracy or longer alignment time. Moreover, chemical cleaving generally requires a long reaction time, which results in a problem that a runtime required per run is long.

PTL 3 discloses a nucleotide where an accuracy of incorporation of the nucleotide can be enhanced and cleaving reaction time can be shortened. By eliminating a leaving group at 3'-oxygen of sugar in the nucleotide, affinity between a polymerase enzyme and the nucleotide is enhanced, thereby an accuracy of incorporation is enhanced. Also, a photocleavable intramolecular linker is introduced to shorten the cleaving time. On the other hand, the nucleotide disclosed in PTL 3 has a problem that an efficiency of photocleaving reaction in a flow cell is still low and thus a read length is not sufficiently long. Since a plurality of reaction cycles is performed in a sequence reaction, a slight difference in reaction efficiency results in a great influence on florescent signals after incorporation when a large number of cycles has been performed. For example, when a reaction efficiency in one cycle is 99%, a florescent intensity after 250 cycles equals 0.99250×100=8.1(%) when a florescent intensity in one cycle is assumed as 100%. Meanwhile, a florescent intensity of 98% results in 0.98250×100=0.6 (%). A mere difference of 1% in reaction efficiency results in a difference of 8.1−0.6=7.5(%) in florescent intensity. A method for enhancing an efficiency of photocleaving reaction may be increasing light intensity. However, there is a problem that too strong light intensity generates a radial due to dissolved oxygen or the like and the radical causes side reactions such as dimerization of a template, thereby reducing the amount of nucleotides incorporated by a primer. When detecting both a top surface and bottom surface of a flow passage as disclosed in PTL 4, light intensity on a surface closer to a light source for photochemical reaction is generally higher than that on a surface farther therefrom. Increasing the light intensity of the light source in order to increase the light intensity on the farther surface results in a light intensity on the closer surface higher than required, thereby causing the aforementioned side reaction.

The present invention provides a flow cell for nucleic acid analysis used for a sequence reaction with photocleavable nucleotides where an efficiency of a cleaving reaction is enhanced.

Solution to Problem

A flow cell for nucleic acid analysis according to the present invention includes: a first substrate provided with an optical filter for reflecting first light for changing a chemical structure of a substance in a flow passage; a hollow sheet having a hollow portion for forming the flow passage; and a second substrate that transmits the first light, where the first substrate, hollow sheet, and second substrate are attached to each other.

Advantageous Effects of Invention

The present invention provides a flow cell for nucleic acid analysis used for a sequence reaction with photocleavable nucleotides where an efficiency of the photocleaving reaction can be enhanced and noise upon florescence detection can be mitigated. This allows for improving the accuracy of sequencing, shortening a runtime, and extending a read length.

DESCRIPTION OF EMBODIMENTS

Figure 1:
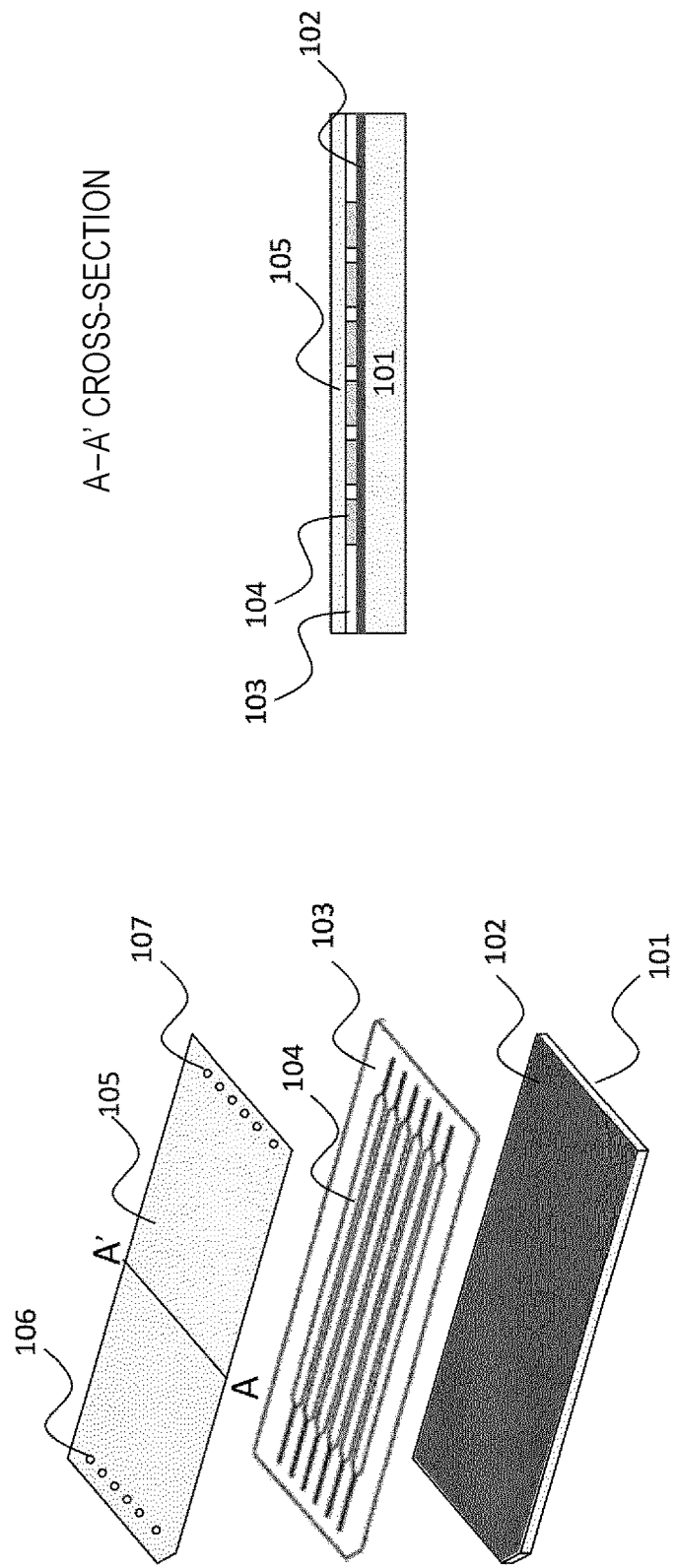
FIG. 1 is a diagram for describing an exemplary configuration of a flow cell for nucleic acid analysis according to the present invention.

Inventors of the present invention have completed, as a result of intensive studies, a flow cell for nucleic acid analysis capable of carrying out a sequence reaction with a high accuracy of nucleotide incorporation, a short cleaving time, and a high efficiency of cleaving.

The present invention includes a flow cell for nucleic acid analysis including: a first substrate provided with an optical filter for reflecting first light for changing a chemical structure of a substance in a flow passage; a hollow sheet having a hollow portion for forming the flow passage; and a second substrate, where the first substrate, hollow sheet, and second substrate are attached to each other. Reflection by the optical filter of the first light having been transmitted by the second substrate results in effective irradiation with the first light of a compound, having an intramolecular linker, on the second substrate or on optical filters on the second substrate and the first substrate from a plurality of directions, thereby enhancing efficiency of a photochemical reaction. A high efficiency of the photochemical reaction allows for improving the accuracy of base sequencing, extending a read length, and shortening a runtime.

Moreover, in the present invention, the optical filter reflects the first light for changing a chemical structure of a substance in the flow passage while transmitting second light for exciting the substance in the flow passage and also transmitting third light irradiated from the substance in the flow passage. This allows for enhancing the efficiency of the photochemical reaction while transmitting, to the outside of the flow cell, excitation light for florescence detection and florescence from noise florescent molecules on the second substrate and the optical filter, thereby reducing noise from florescent molecules other than those of target colonies. The noise florescent molecules, upon detection of colonies on the second substrate, include florescent molecules attached to a region other than the colonies on the second substrate as well as florescent molecules carried over in the flow passage or florescent molecules on the optical filter of the first substrate. The noise florescent molecules upon detection of colonies on the optical filter of the first substrate include, in addition to those on the optical film, molecules carried over in the flow passage or molecules on the second substrate.

Also, in the present invention, the optical filter is patterned and the patterned optical filter is disposed on a surface, of the first substrate, in contact with the flow passage. Generally, the optical filter includes multi-layered thin films of inorganic oxides or metal oxides formed by a method such as vapor deposition and is flatter than a normal glass. Therefore, the optical filter has a low adhesion power to the hollow sheet of polyimethylsiloxane (PDMS), a pressure-sensitive double-sided adhesive tape or the like, resulting in a problem of low withstanding pressure of the flow cell. Patterning of the optical filter allows for a structure where the hollow sheet and the first substrate of glass or the like with a high adhesion power are in direct contact, thereby enhancing the withstanding pressure of the flow cell.

Moreover, in the present invention, the second substrate includes a near-ultraviolet ray cut filter for transmitting the first light for changing a chemical structure of a substance in the flow passage while reflecting fourth light having a wavelength shorter than that of the first light. Generally, DNA absorbs light having a wavelength of 320 nm or less and a part thereof is dimerized, which results in decreased reaction efficiency of the sequence reaction. Also, it is known that near-ultraviolet rays having a wavelength of 184.9 nm generates ozone and generated ozone is decomposed by ultraviolet rays having a wavelength of 253.7 nm and results in oxygen atoms having a strong oxidation power. These ozone or oxygen atoms oxidatively decompose polymerases, nucleotides, or the template used in the sequence reaction, thereby decreasing the reaction efficiency of the sequence reaction. The near-ultraviolet ray cut filter according to the present invention prevents such near-ultraviolet rays from being transmitted into the flow passage.

Furthermore, in the present invention, the second substrate has an antireflection film preventing reflection of the first light and second light. Generally, it is known that a glass surface reflects less than 10% of light. The antireflection film according to the present invention prevents reflection of the first light or second light by a surface of the substrate, thereby minimizing a decrease in light intensity of the first light or second light entering the flow passage.

Figure 7:
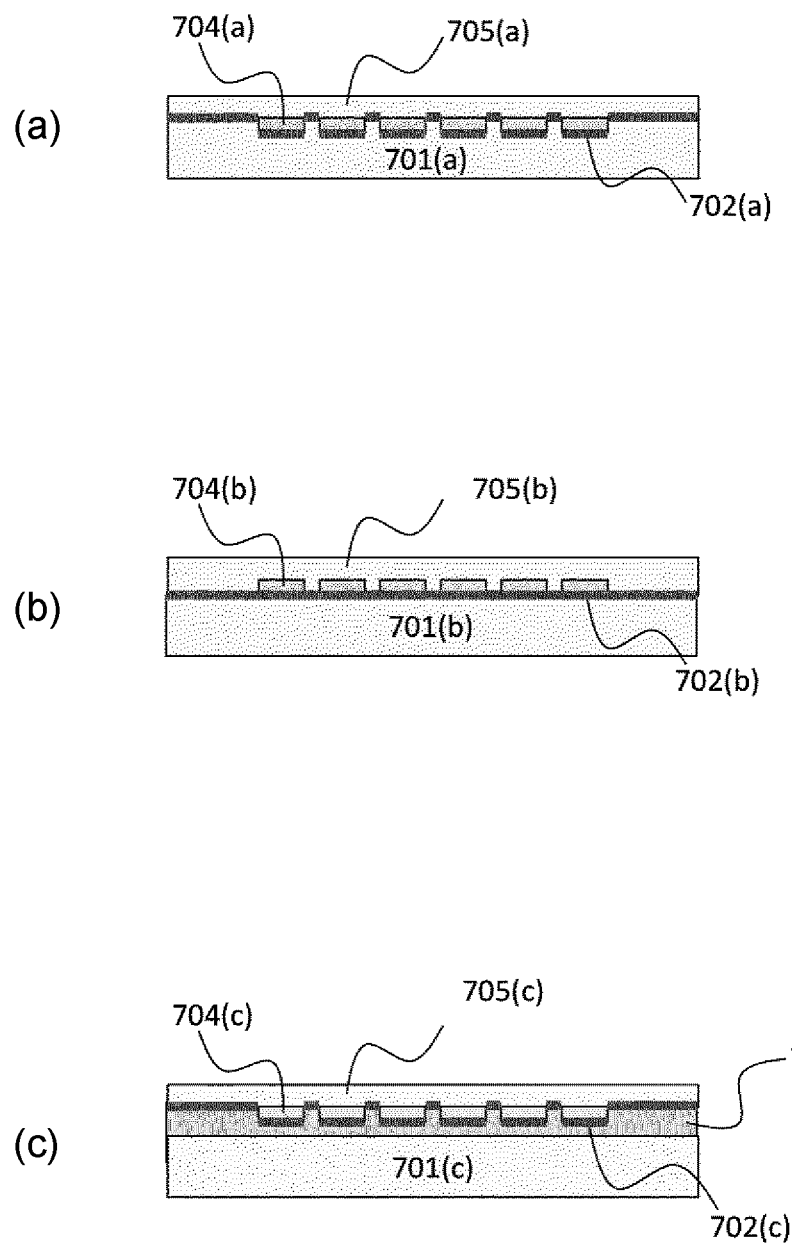
FIGS. 7($a$) to 7($c$) are diagrams for describing an exemplary configuration of a flow cell for nucleic acid analysis according to the present invention.

Also, in the present invention, in the flow cell for nucleic acid analysis including the first substrate and second substrate attached to each other or the first substrate, second substrate, and a grooved sheet attached to each other, the first light for changing a chemical structure of a substance in a flow passage is transmitted by the second substrate and an optical filter for reflecting the first light is included on a bottom surface of the flow passage opposite to the second substrate across the flow passage. Even in a structure without the hollow sheet as illustrated in FIGS. 7(a) to 7(c), similar effects can be obtained with a similar mechanism as described above.

Also, in the present invention, in the flow cell for nucleic acid analysis including the first substrate and second substrate attached to each other or the first substrate, second substrate, and a grooved sheet attached to each other, the optical filter reflects the first light for changing a chemical structure of a substance in a flow passage, transmits the second light for exciting the substance in the flow passage, and also transmits the third light irradiated from the substance in the flow passage. Similarly to the above, even in a structure without the hollow sheet as illustrated in FIGS. 7(a) to 7(c), similar effects can be obtained with a similar mechanism as described above.

Hereinafter, the above and other novel characteristics and effects of the present invention will be described with reference to the drawings.

Here, although specific embodiments are described in detail to facilitate complete understanding of the present invention, the present invention is not limited to the contents described herein. Also, each of the embodiments may be combined as appropriate. The present description also discloses such combinations.

Example 1

An exemplary flow cell for nucleic acid analysis according to the present invention is illustrated in FIG. 1.

The flow cell for nucleic acid analysis according to the present invention has a configuration where a first substrate 101 having an optical filter 102, a hollow sheet 103 having a hollow portion 104 for forming a flow passage, and a second substrate 105 are attached to each other. A space enclosed by the optical filter 102 on the first substrate, the hollow sheet 103, and the second substrate 105 forms the flow passage. A hole made on the second substrate forms an inlet 106 for injecting liquid into the flow passage or an outlet 107. In the exemplary flow cell for nucleic acid analysis in FIG. 1, the second substrate includes the holes; however, the first substrate may include holes, which may be the inlet or outlet.

Figure 10:
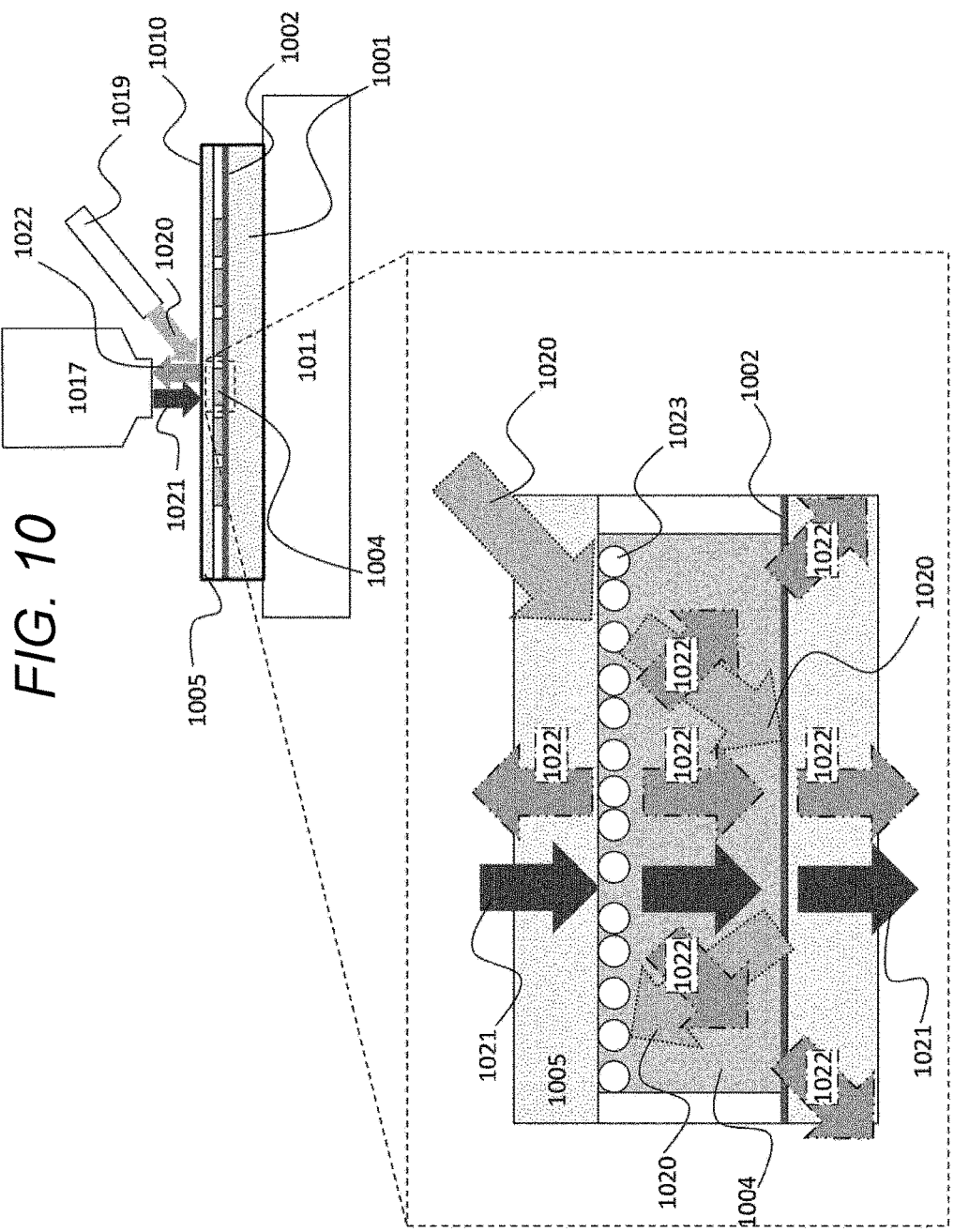
FIG. 10 is a diagram for describing an exemplary nucleic acid analyzer according to the present invention.

FIG. 10 illustrates a configuration where a flow cell for nucleic acid analysis 1010 according to the present invention is mounted to a nucleic acid analyzer. A light source 1019 emits first light 1020 for changing a chemical structure of a target substance in a flow passage. A detection unit 1017 emits second light 1021 for exciting the substance in the flow passage and detects third light 1022 irradiated from the excited substance in the flow passage. In the example in FIG. 10, a bead carrier 1023 carries, on a surface thereof, a plurality of molecules of the target substance in the flow passage. A holder unit 1011 holds the flow cell for nucleic acid analysis 1010. The first light 1020 emitted from the light source 1019 passes through a first substrate 1020 and then irradiates the substance in the flow passage carried on the bead carrier 1023. A part of the first light 1020 transmitted by the bead carrier 1023 is reflected by an optical filter 1002. The reflected first light 1020 irradiates a lower surface of the bead carrier 1023, thereby enhancing the efficiency of the photoreaction of the substance in the flow passage in the lower side of the bead carrier 1023. The second light 1021 having passed the second substrate 1005 excites the substance in the flow passage on the bead carrier 1023. The second light 1021 having passed the bead carrier 1023 is transmitted by the optical filter 1002 and travels outside a flow passage 1004. The target substance in the flow passage in the sequence reaction is a nucleotide having an intramolecular florescent molecule via a photocleavable linker. The sequence reaction is performed by, generally, introducing an amplification template on the bead carrier 1023 outside the flow cell for nucleic acid analysis 1010, then fixing the bead carrier 1023 having the amplification template on the second substrate in contact with the flow passage, thereby hybridizing the amplification template with a sequence primer. After the hybridization, an aqueous solution containing the nucleotides and enzyme is supplied to the flow passage 1004 to allow the primer to incorporate the nucleotides. Thereafter, the flow passage 1004 is washed, thereby removing unreacted nucleotides. After removing the unreacted nucleotides, the incorporated nucleotides are irradiated with the first light 1020 to allow a photocleaving reaction to be carried out. The flow passage 1004 is then washed. Here, remaining nucleotides without being removed upon washing the flow passage become noise when detecting florescence. In the same manner, remaining florescent dyes after photocleaving become noise. The nucleotides or florescent dyes after photocleaving remain on the surface of the bead carrier 1023, on a surface of the second substrate 1005 in contact with the flow passage 1004, or on the optical filter 1002 in contact with the flow passage 1004. The optical filter according to the present invention allows the second light 1021 to travel outside the flow passage. Therefore, noise derived from the remaining nucleotides or florescent dyes after photocleaving can be mitigated. Meanwhile, the optical filter 1002 also allows the third light 1022 generated by excitation by the second light 1021 to travel outside the flow passage 1004. Although FIG. 10 illustrates an example where the bead carrier 1023 is fixed only to a top surface of the flow passage, in an example where the bead carrier 1023 is also fixed to the optical filter 1002, the third light 1022 from the bead carrier 1023 on the lower surface of the flow passage or the third light 1022 from the nucleotides remaining in the flow passage or from the florescent dyes after photocleaving becomes noise upon detection of the top surface of the flow passage. However, the optical filter 1002 according to the present invention allows such third light 1022 to travel outside the flow passage 1004, thereby mitigating noise. Here, applying, on the holder unit, an organic matter capable of absorbing the second light or third light prevents the second light or third light having once traveled outside the flow passage 1004 from being reflected by a surface of the holder unit and returning into the flow passage 1004, thereby further mitigating noise.

A wavelength of the first light is not limited as long as a linker, in the nucleotide having an intramolecular florescent molecule via the photocleavable linker, can be cleaved. Meanwhile, a wavelength of 450 nm or less is desirable since such a wavelength can cleave the nucleotides described in PTL 3 and does not overlap with a second wavelength for exciting general florescent molecules. Moreover, a wavelength greater than 320 nm is desirable since such a wavelength prevents dimerization of DNA due to radical generation.

A wavelength of the second light is not limited as long as florescent molecules can be excited. Meanwhile, since the sequence reaction requires four types of florescent dyes to be used simultaneously for detection, a wavelength of 450 nm or more is desirable since such a wavelength allows for easy selection of dyes where an overlap of light emitting wavelengths among dyes in four colors can be minimized. A wavelength of the third light is not specifically limited either. Meanwhile, similarly to the wavelength of the second light, a wavelength of 480 nm or more is desirable since such a wavelength allows for easy selection of dyes where an overlap of light emitting wavelengths among dyes in four colors can be minimized. To achieve a combination of dyes where an overlap of the second light wavelength of 450 nm or more, the third light wavelength of 480 nm or more, and the light emitting wavelengths of dyes in four colors can be minimized, it is only required to select one dye from each of groups including: a first group including Alexa Fluor488, FAM, FITC, and Oregon Green488, a second group including AlexaFluor532, BODIPY TMR-X, Cy3, HEX, and JOE, a third group including Alexa Fluor594 and TexasRed-X, and a fourth group including BODIPY 650/665 and Cy5 and to combine the selected dyes.

A material of the first substrate 101 used in the present invention is not specifically limited. Inorganic materials such as glass, sapphire, and silicone, metals such as aluminum and copper, alloys such as stainless steel, or resin materials such as polymethylmethacrylate resin, polycarbonate resin, and cyclolefinic resin may be used. Meanwhile, when the flow cell is used for the sequence reaction, since the holder unit 1011 in contact with the first substrate 1001 has a temperature adjusting function, those having a high heat conductivity is desirable such as glass, silicone, stainless steel, carbon fiber, or a resin material with a high heat conductivity where an inorganic filler is blended. A desirable thickness, where heat conductivity is maintained and a strong flow cell can be obtained after attachment, is 0.1 mm or more and 100 mm or less.

A material of the second substrate 102 is not specifically limited as long as light is transmitted. Inorganic materials such as glass, sapphire, and quartz or resin materials such as acrylic resin and cyclolefinic resin may be used. A desirable thickness is 0.1 mm or more and 10 mm or less conforming to a specification of an object lens mounted to the detection unit 1017.

A material of the hollow sheet 203 is not specifically limited while thermosetting or photosetting epoxy adhesives or acrylic adhesives may be used. Alternatively, a double-sided tape including mainly acrylic resin may be used. More preferable material may be glass, quartz, sapphire, or polydimethylsiloxane having a high adhesive strength to transparent resins. A thickness of a spacer is not specifically limited while a thinner spacer allows for reducing the capacity of the flow passage, thereby reducing an amount of reagent used. A thickness of a spacer 506 is preferably 1 mm or less.

Figure 11:
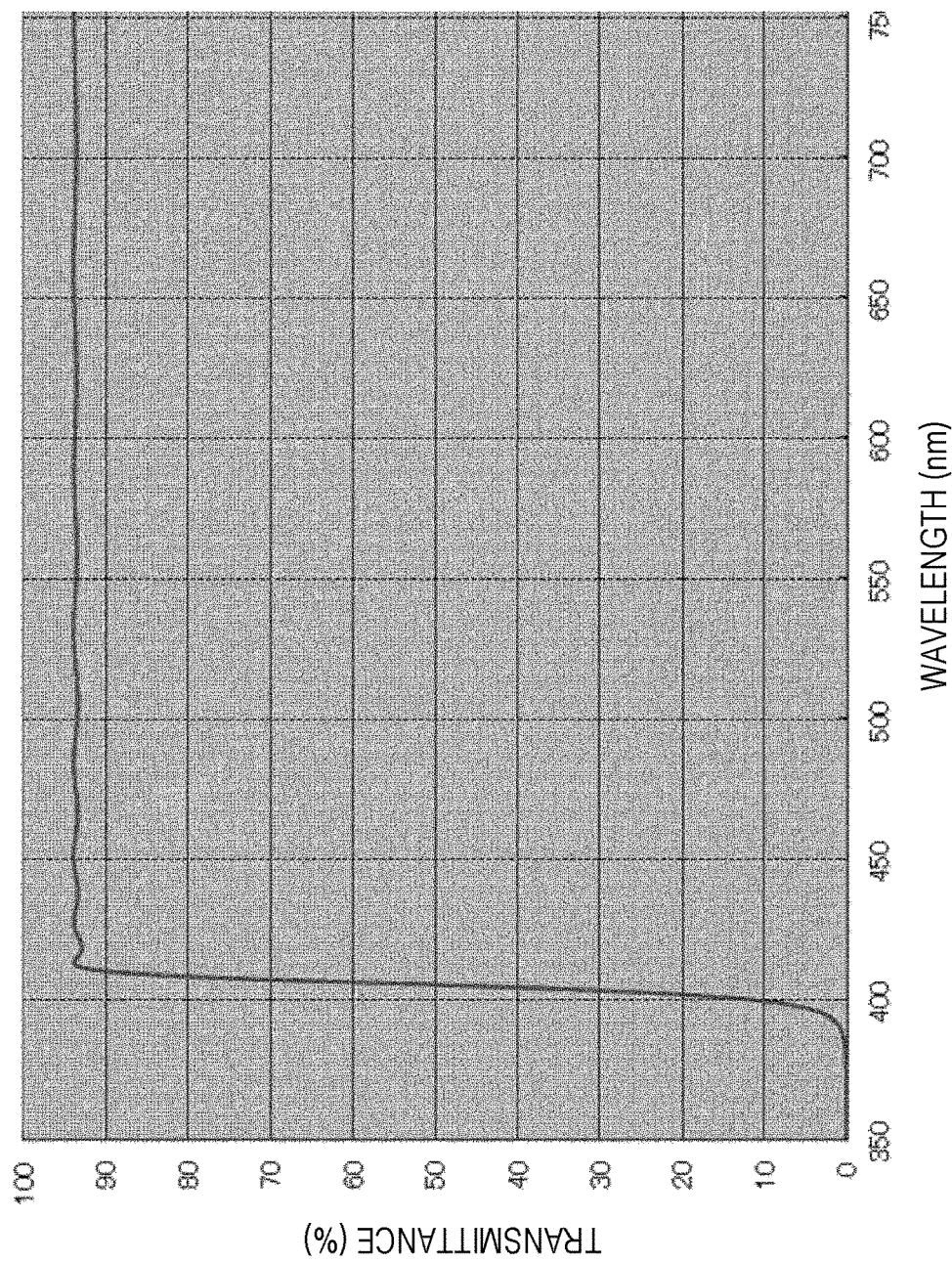
FIG. 11 is a diagram for describing an exemplary configuration of a flow cell for nucleic acid analysis according to the present invention.

The optical filter 104 is manufactured by laminating a dielectric multilayer film of SiO2, TiO2, Ta2O2, Nb2O3 or the like for about ten to forty layers and is capable of reflecting light of a desired wavelength while transmitting light of other wavelengths. FIG. 11 illustrates optical characteristics of an optical filter suitable for the present invention. The optical filter reflects the first light having a wavelength of less than 400 nm and transmits the second light and third light having a wavelength of 400 nm or more. Also, as illustrated in FIGS. 1 and 3 to 7, a structure where the optical filter is provided on the top surface of the first substrate can prevent the optical filter 1002 from directly being in contact with the holder unit 1011 when mounting the flow cell for nucleic acid analysis 1001 to the holder unit 1011, thereby preventing occurrence of a flaw on the optical filter. Furthermore, using SiO2 on the outermost surface of the optical filter can prevent a material such as Al2O3 and TiO2 included in the multilayer film from being in contact with a buffer including chlorine ion used in the sequence reaction, thereby preventing corrosion of such an oxide film.

Figure 2:
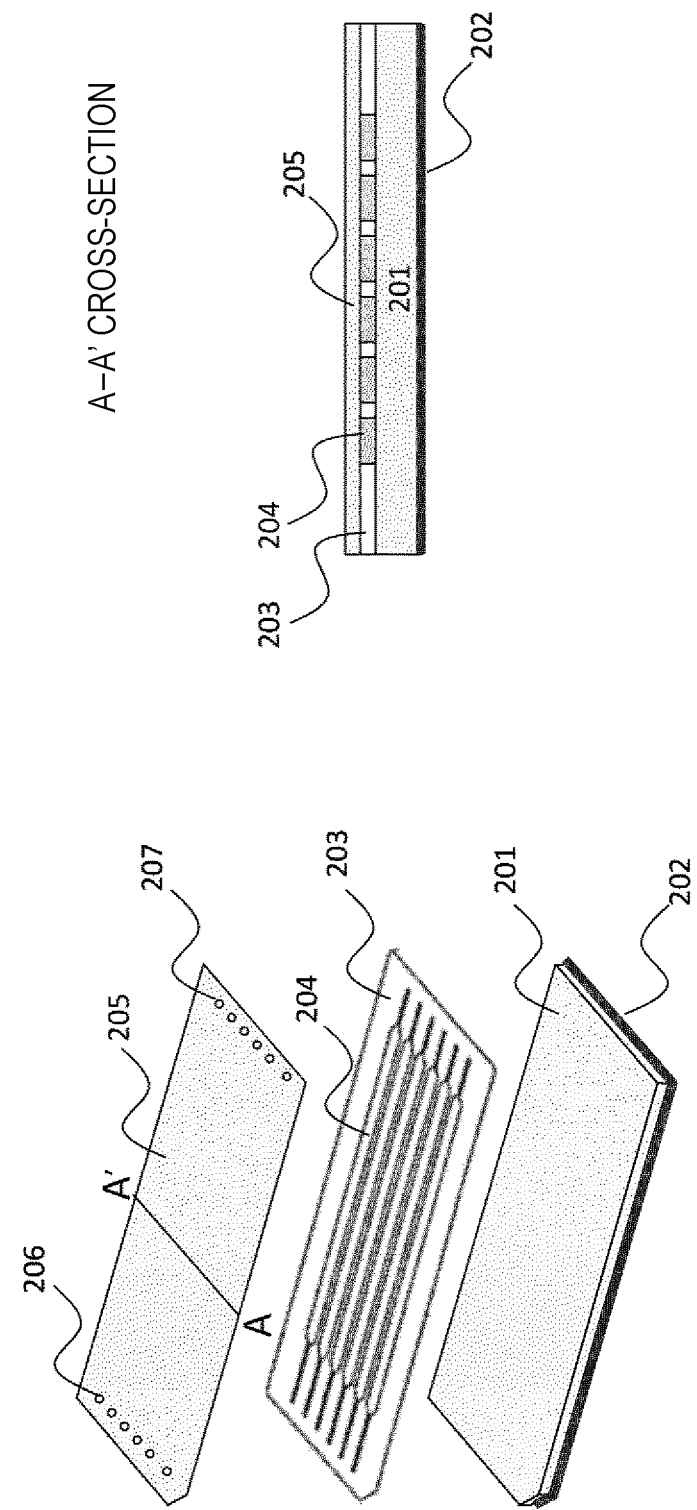
FIG. 2 is a diagram for describing an exemplary configuration of a flow cell for nucleic acid analysis according to the present invention.
Figure 3:
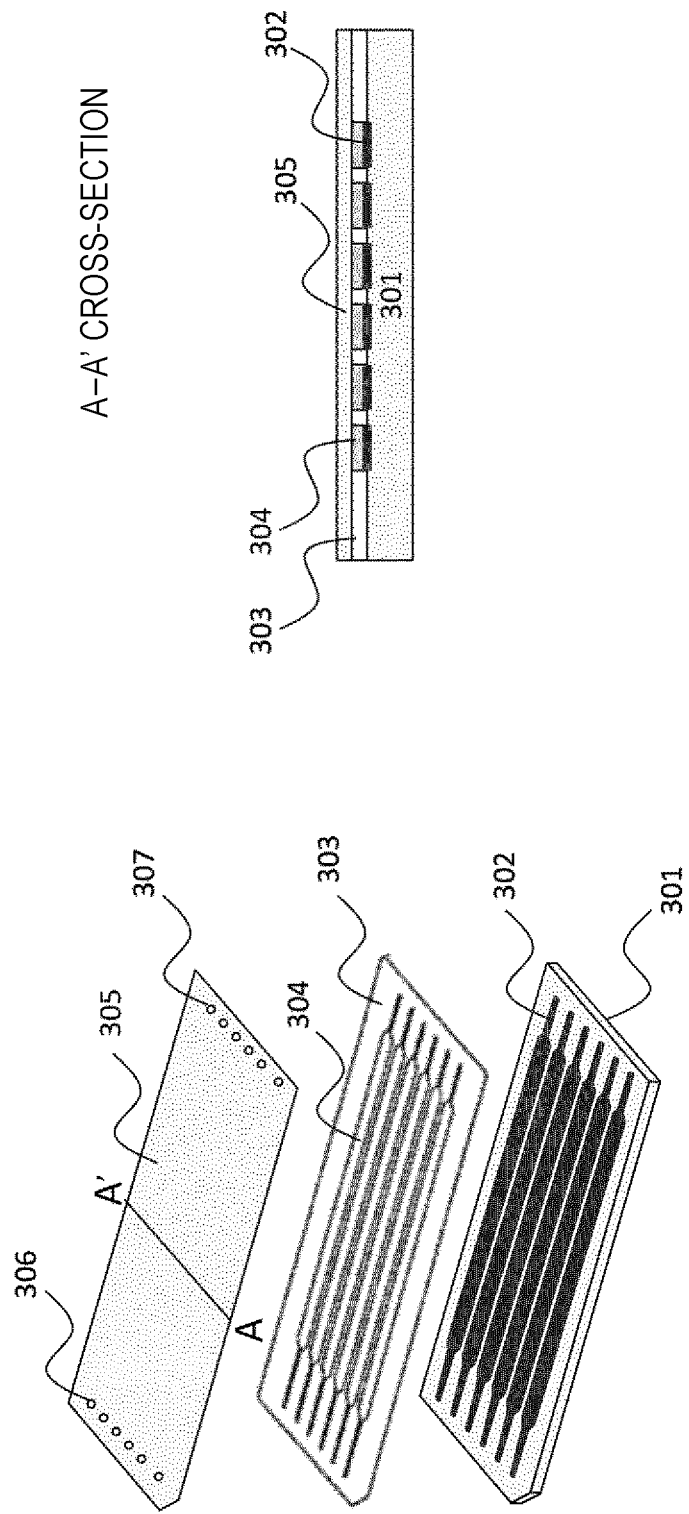
FIG. 3 is a diagram for describing an exemplary configuration of a flow cell for nucleic acid analysis according to the present invention.
Figure 4:
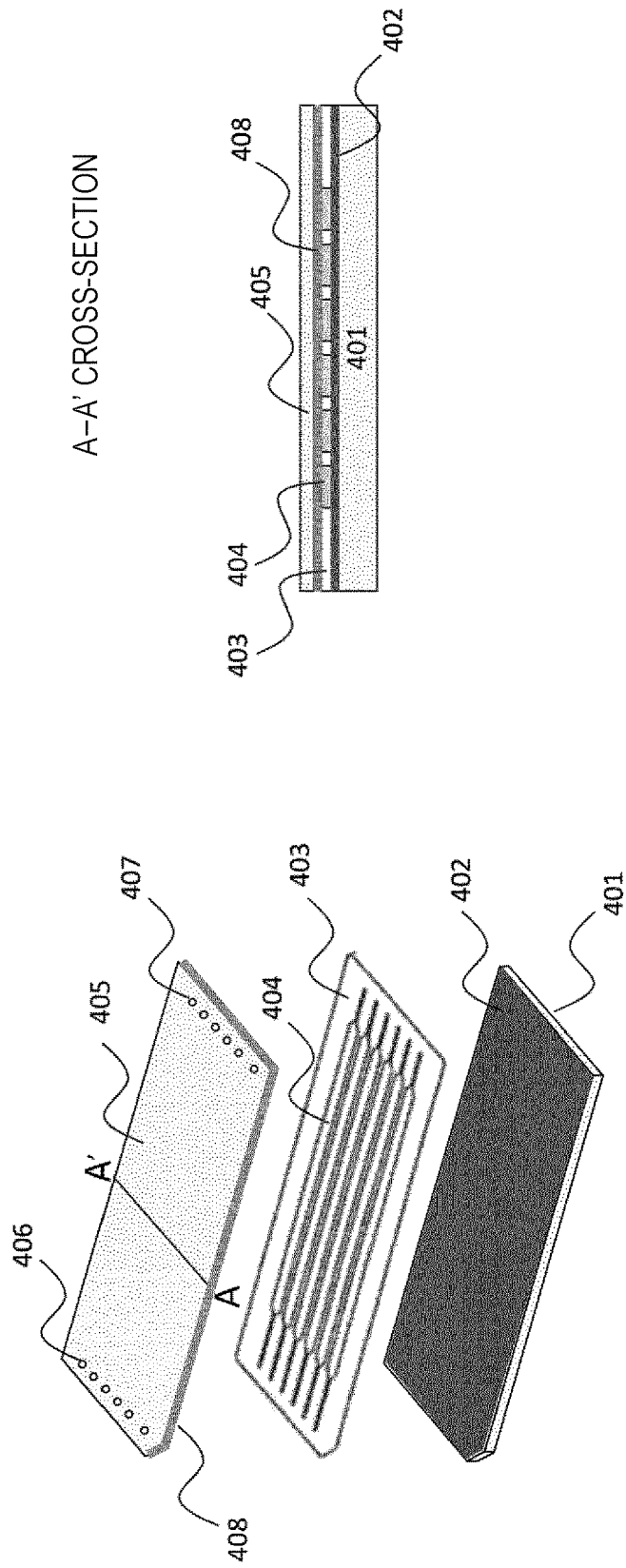
FIG. 4 is a diagram for describing an exemplary configuration of a flow cell for nucleic acid analysis according to the present invention.
Figure 5:
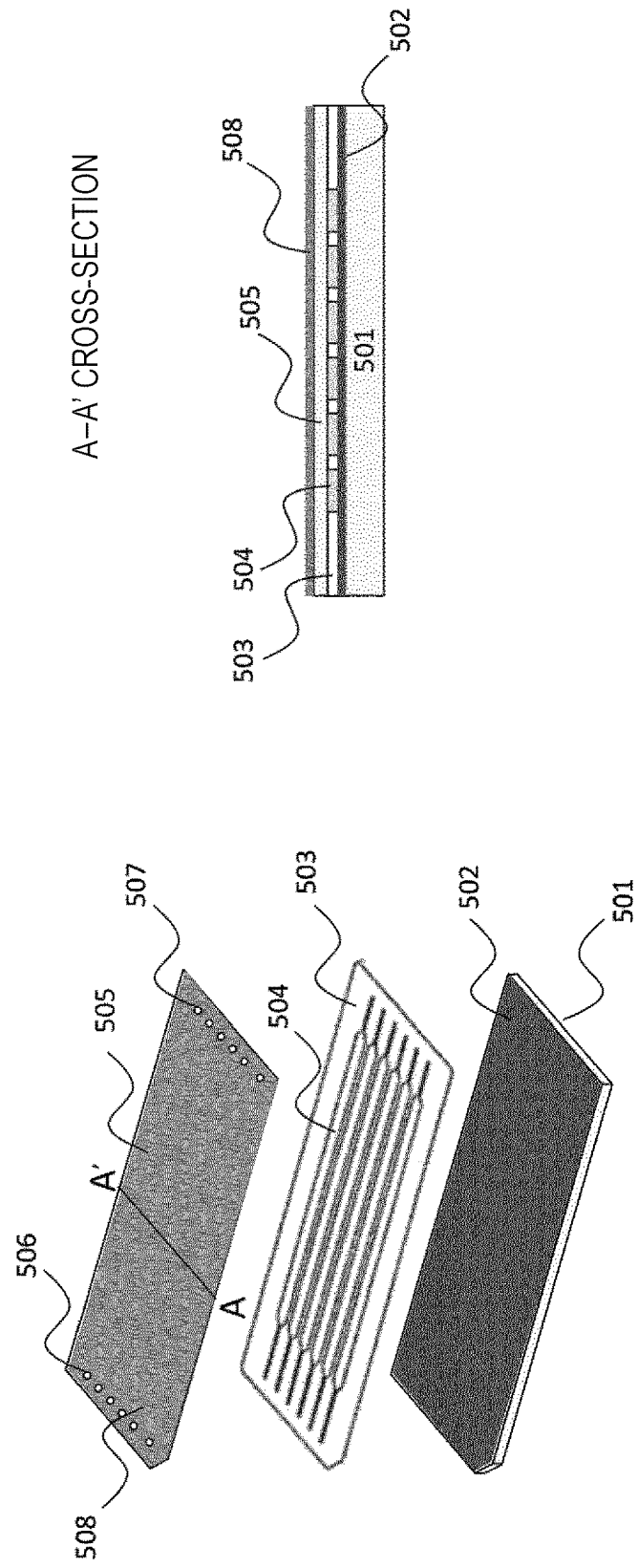
FIG. 5 is a diagram for describing an exemplary configuration of a flow cell for nucleic acid analysis according to the present invention.
Figure 6:
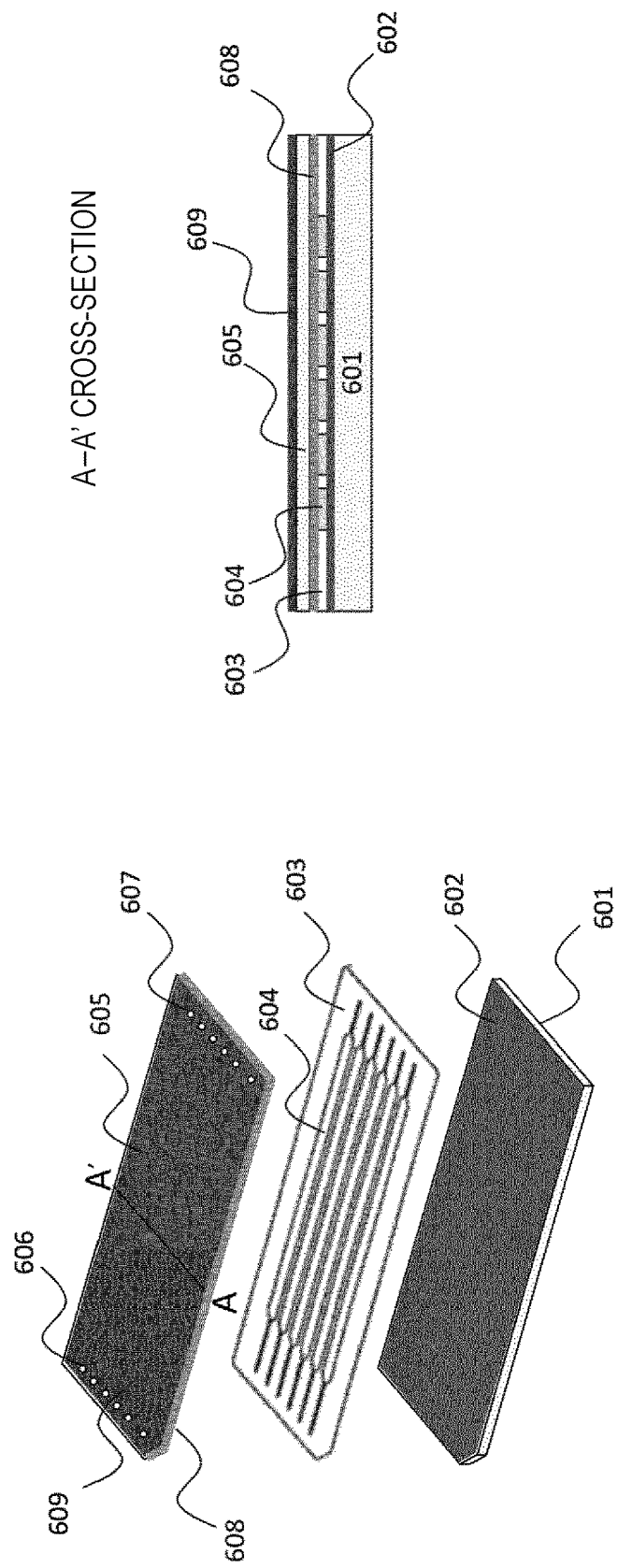
FIG. 6 is a diagram for describing an exemplary configuration of a flow cell for nucleic acid analysis according to the present invention.
Figure 12:
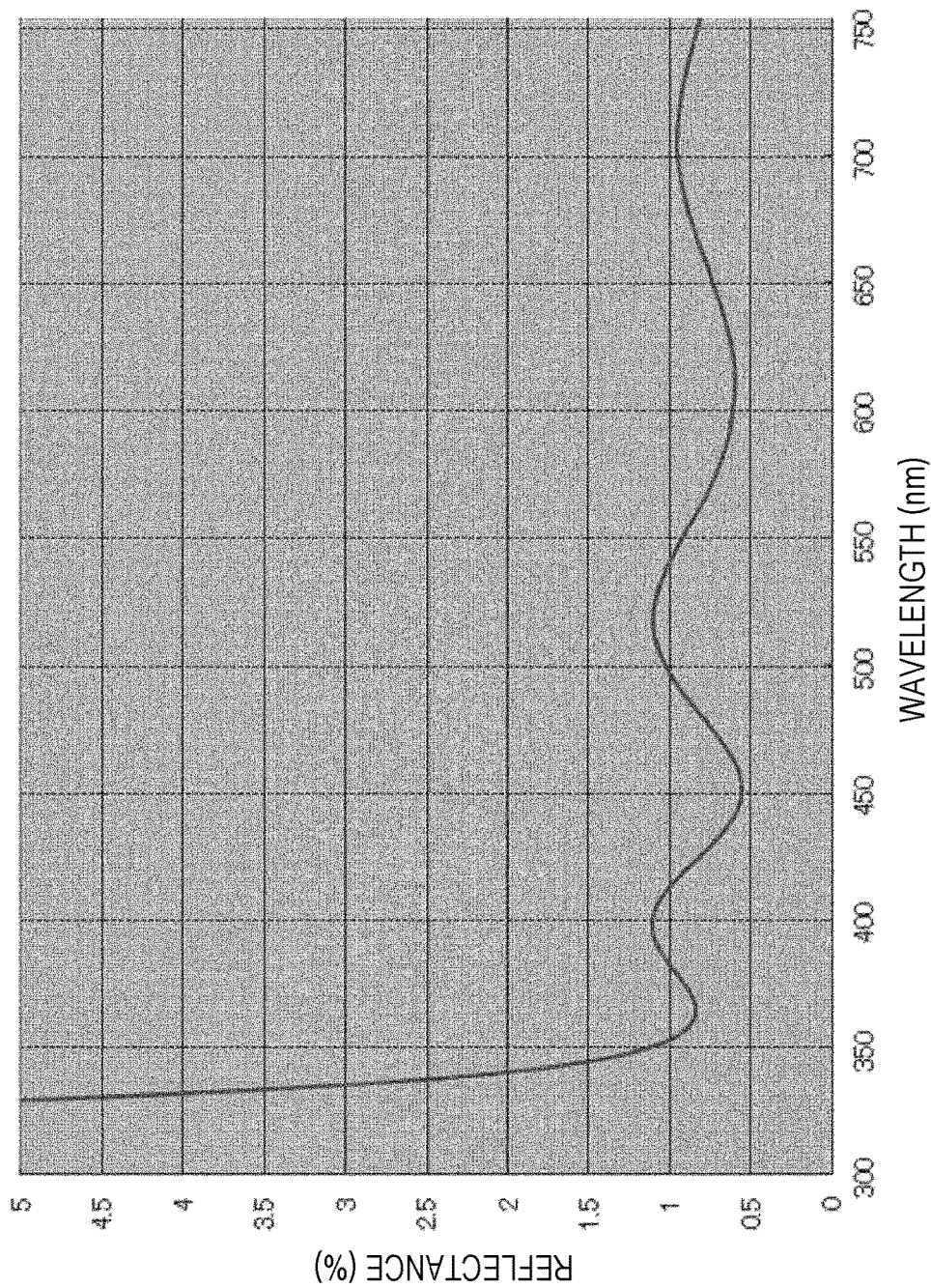
FIG. 12 is a diagram for describing an exemplary configuration of a flow cell for nucleic acid analysis according to the present invention.

FIGS. 2 to 7 illustrate other configurations of flow cells for nucleic acid analysis according to the present invention. FIG. 2 illustrates a flow cell for nucleic acid analysis where an optical filter 202 is provided on a lower surface of a first substrate 201. FIG. 3 illustrates a flow cell for nucleic acid analysis where a patterned optical filter 302 is disposed, on a first substrate, to be in contact with a flow passage. Generally, an optical filter is flatter than a normal glass and thus has a low adhesion power to a hollow sheet of polyimethylsiloxane (PDMS), a pressure-sensitive double-sided adhesive tape or the like, resulting in a problem of low withstanding pressure of the flow cell. The flow cell for nucleic acid analysis in FIG. 2 or 3 has a structure where the hollow sheet and the first substrate of glass or the like with a high adhesion power are in direct contact, thereby enhancing the withstanding pressure of the flow cell. A flow cell for nucleic acid analysis in FIG. 4 or 5 is provided with, on a second substrate, a near-ultraviolet filter for reflecting near-ultraviolet rays having a wavelength of 320 nm or less. The near-ultraviolet filter prevents near-ultraviolet rays from entering the flow passage. Generally, DNA absorbs light having a wavelength of 320 nm or less and a part thereof is dimerized, which results in decreased reaction efficiency of the sequence reaction. Also, it is known that near-ultraviolet rays having a wavelength of 184.9 nm generates ozone and generated ozone is decomposed by ultraviolet rays having a wavelength of 253.7 nm and results in oxygen atoms having a strong oxidation power. These ozone or oxygen atoms oxidatively decompose polymerases, nucleotides, or the template used in the sequence reaction, thereby decreasing the reaction efficiency of the sequence reaction. The flow cell for nucleic acid analysis in FIG. 4 or 5 prevents a decrease in an efficiency of the sequence reaction due to near-ultraviolet rays. A flow cell for nucleic acid analysis in FIG. 6 is provided with an antireflection film 609 on a second substrate 605. The antireflection film 609 prevents reflection of the first light 1020 or second light 1021 by a top surface of the second substrate, thereby minimizing a decrease in light intensity of the first light 1020 or second light 1021 entering a flow passage 604. Generally, it is known that visible light having a wavelength of 400 nm to 800 nm is reflected on a glass surface by less than 10% thereof. FIG. 12 illustrates optical characteristics of the antireflection film according to the present invention. A reflectance can be suppressed to 2% or less. Such an antireflection film may be formed by a multilayer film including Al, MgF2, SiO2, and Al2O3. In a flow cell for nucleic acid analysis in FIGS. 7(a) to 7(c) including a first substrate and second substrate attached to each other or the first substrate, second substrate, and a grooved sheet 720 attached to each other, the first light for changing a chemical structure of a substance in a flow passage is transmitted by the second substrate and an optical filter for reflecting the first light is provided on a bottom surface of the flow passage opposite to the second substrate across the flow passage. Even in a structure without a hollow sheet as illustrated in FIGS. 7(a) to 7(c), similar effects can be obtained. Such a flow cell can be fabricated by using: glass or etched glass for the second substrate; etched silicone or PDMS for the grooved sheet; and glass or silicone for the first substrate.

Figure 8:
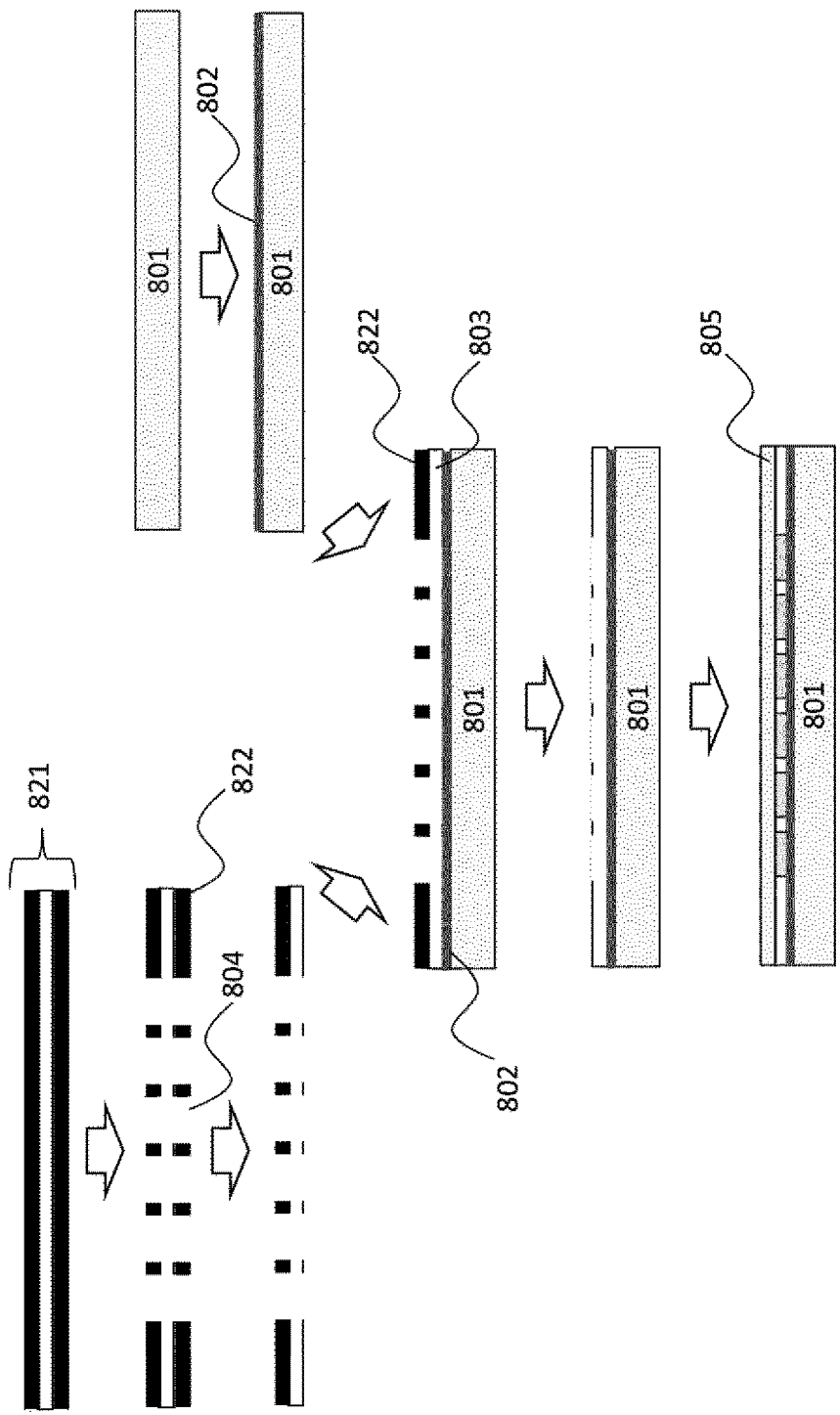
FIG. 8 is a diagram for describing an exemplary manufacturing method of a flow cell for nucleic acid analysis according to the present invention.

An exemplary manufacturing method of the flow cell for nucleic acid analysis according to the present invention will be described with FIG. 8. A protective film-attached sheet 821 having a mold-releasable protective film is subjected to punching press working or laser processing to make a hollow portion therein, thereby forming a hollow portion 804 that forms a flow passage. Next, an optical film 802 is formed on a first substrate 801 by vapor deposition or the like. A protective film 822 is removed from the protective film-attached sheet 821 and then the protective film-attached sheet removed of the protective film 822 and the first substrate 801 having the optical film 802 are attached to each other. A surface of the optical film 802 and a surface of the hollow sheet may be exposed to excimer, oxygen plasma, or atmospheric pressure plasma before attachment in order to enhance an adhesion power between the optical film 802 and the hollow sheet 803. Also, heating processing may be performed after attachment in order to enhance the adhesion. Next, after removing the remaining protective film 822, the hollow sheet 803 is attached to the second substrate 805. The hollow sheet 803 may be exposed to the aforementioned excimer, oxygen plasma, or atmospheric pressure plasma or be subjected to heating processing in order to enhance an adhesion power between the second substrate 805 and the hollow sheet 803.

The flow cell for nucleic acid analysis having been fabricated in this manner is mounted to a nucleic acid analyzer for performing nucleic acid analysis. The present invention also includes a nucleic acid analyzer for performing a nucleic acid reaction by mounting the flow cell for nucleic acid analysis according to the present invention. The nucleic acid analyzer according to the present invention at least includes: a holder unit for holding the flow cell for nucleic acid analysis; a detection unit for observing a sample in the flow cell for nucleic acid analysis; a light source for irradiating the flow cell for nucleic acid analysis with first light for changing a structure of a substance in the flow passage; and a liquid feeding unit for feeding a reagent to the flow cell for nucleic acid analysis.

Figure 9:
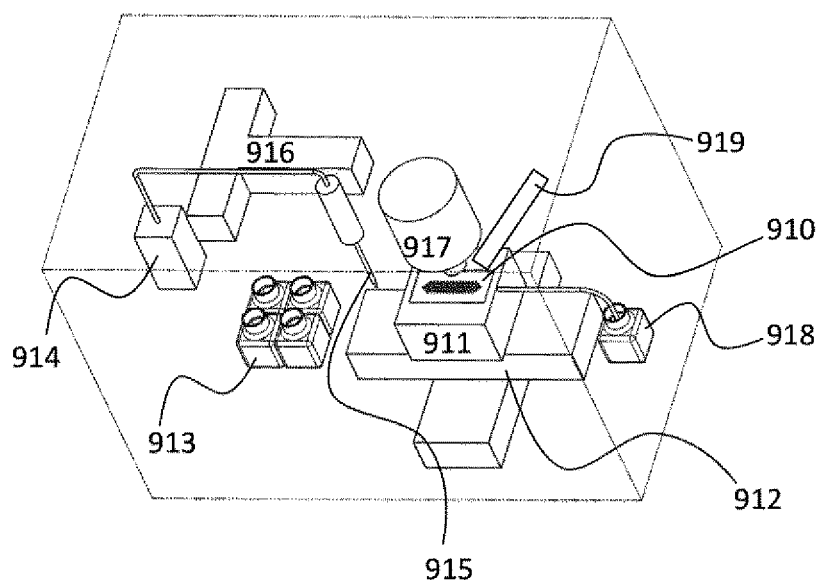
FIG. 9 is a diagram for describing an exemplary nucleic acid analyzer according to the present invention.

An exemplary nucleic acid analyzer according to the present invention will be described with FIG. 9. The nucleic acid analyzer includes: a flow cell for nucleic acid analysis 910 according to the present invention; a holder unit 911 capable of fixing the flow cell for nucleic acid analysis 910 and adjusting the temperature of the flow cell for nucleic acid analysis 910; a stage unit 912 for moving the flow cell for nucleic acid analysis 910 and the holder unit 911; a reagent container 913 containing a plurality of reagents and washing water; a liquid feeding unit 914 which is a driving source for sucking the reagent accommodated in the reagent container 913 and injecting the reagent into the flow cell for nucleic acid analysis 910; a nozzle 915 for actually accessing the reagent container 913 or flow cell for nucleic acid analysis 910 upon sucking or discharging the reagent; a nozzle transfer unit 916 for transferring the nozzle 915; a detection unit 917 for observing a sample fixed to the flow cell for nucleic acid analysis 910; a light source 919 for emitting first light for changing a structure of a substance in the flow passage; and a waste liquid container 918 for accommodating waste liquid. The detection unit 917 includes, for example, a florescence detector and is capable of irradiating the flow cell for nucleic acid analysis 910 on the stage unit with excitation light and detecting generated florescence.

The nucleic acid analyzer according to the present invention operates as described below. First, the flow cell for nucleic acid analysis 910 holding a target sample nucleic acid is mounted to the holder unit 911. Next, the nozzle 916 accesses the reagent container 913 and sucks the reagent with the liquid feeding unit 914. The nozzle 915 is transferred to a top surface of the flow cell for nucleic acid analysis 910 by the nozzle transfer unit 916 and then injects the reagent into the flow cell for nucleic acid analysis 910. Thereafter, the holder unit 911 adjusts the temperature of the solution contained in the flow passage of the flow cell for nucleic acid analysis 910, thereby controlling the sequence reaction. To observe the sample nucleic acid having been reacted, the flow cell for nucleic acid analysis 910 is moved by the stage unit 912 to be irradiated with the excitation light. A plurality of types of florescence from the sample nucleic acid in a detection region is then detected. Here, it is preferable that the excitation light is irradiated through the substrate on a side where the sample nucleic acid or the carrier, having the sample nucleic acid thereon, is fixed to for detecting the florescence. The flow cell for nucleic acid analysis 910 is slightly moved and detection in a similar manner is repeated a plurality of times. When the observation finishes in all of the detection regions, the washing water accommodated in the reagent container 913 is sucked by the liquid feeding unit 914 and injected into the flow cell for nucleic acid analysis 910, thereby washing inside the flow passage of the flow cell for nucleic acid analysis 910. Next, another reagent is injected and then the first light is irradiated to the substance in the flow passage having been incorporated to the sample nucleic acid, thereby changing the structure of the substance in the flow passage so that a reaction of a next cycle proceeds. Thereafter, the inside of the flow passage of the flow cell for nucleic acid analysis 910 is washed in a similar manner. A cycle of injection of the reagent, the sequence reaction under temperature control, florescence detection, washing inside the flow passage, irradiation with the first light, and washing inside the flow passage is repeated a plurality of times. This allows or reading the sample nucleic acid. The nucleic acid analyzer is controlled by a computer and is capable of performing the aforementioned operations automatically.

Example 2

An exemplary method of nucleic acid analysis using the nucleic acid analyzer according to the present invention will be described. The analysis method conforms to a method disclosed in Science 2005, vol. 309, pp. 1728-1732 (NPL 2).

(1) Library Preparation

A target substance in the flow passage was purified with Dneasy Tissue kit (QIAGEN) and then a sample nucleic acid was frangmentated. With the fragmented DNA, both terminals of a template DNA was added with a tag sequence with End-it DNA End Repair kit (EpiCentre). The template having been added with the tag sequence was purified and then added with a spacer sequence, which was then processed with exonuclease, thereby preparing a template for rolling circle amplification (RCA). With the obtained template, RCA was performed with random hexamer, thereby amplifying the template. Amplification product was purified by Microcon-30 (Millipore) and then fragmentated by a restriction enzyme. The fragmentated product was subjected to gel purification. A tag library of 70 base lengths was extracted. The tag library having been extracted was subjected to ligation with a primer and then to PCR amplification, thereby preparing a library.

(2) Emulsion PCR

A PCR solution, MyOne (trademark), paramagnetic streptavidin magnetic beads (Dynal), and a solution of the library were added to an oily solution of Light mineral oil (Sigma) and then emulsion PCR was performed. A solution containing a surfactant was added to an amplification solution, which was then subjected to high-speed centrifugation. Thereafter, solvent displacement was performed with a magnet and an aqueous solution of beads, having, on a surface thereof, DNA for measurement having a number of amplification products on a surface thereof, was prepared.

(3) Fixing Beads Having DNA on a Surface Thereof to the Flow Cell for Nucleic Acid Analysis Beads ($4.2 \times 10^7$ in number) were dispersed in a TE buffer containing 19.2 µl of 10 mM sodium dodecyl sulfate. The bead-dispersed solution was then injected into the flow cell for nucleic acid analysis. The bead suspension in the flow passage was dried in a thermostatic chamber and then a 6% aqueous solution of acrylamide was injected into the flow passage to fix the beads thereto. Although the beads were fixed using acrylamide in the present example, the beads may be fixed by using a bonding between silane and polylysine or a bonding between biotin and streptavidin or the like as disclosed in PTL 5.

(4) Nucleic Acid Analysis

Nucleic acid analysis was performed with a nucleotide disclosed in PTL 3. The flow cell for nucleic acid analysis where the beads had been fixed was mounted to the nucleic acid analyzer according to the present invention. An aqueous solution containing the primer was injected into the flow cell for nucleic acid analysis 910 via the nozzle 915. The aqueous solution in the flow cell for nucleic acid analysis 910 was heated to 57° C. using the holder unit 911, and thereafter maintained at 4° C. An aqueous solution containing the aforementioned nucleotide and DNA polymerase was injected to the flow cell for nucleic acid analysis 910, which thereafter was maintained at 60° C. for five minutes to allow an elongation reaction to be carried out. The flow passage of the flow cell for nucleic acid analysis 910 was washed with a buffer and unreacted nucleotides were removed. The flow cell for nucleic acid analysis 910 was moved by the stage unit 912 and then irradiated with the excitation light by the detection unit 917. A plurality of types of florescence having been introduced to the beads attached with the sample nucleic acid in a detection region was detected. After detection, an aqueous solution of 50 mM sodium azide was injected and florescent dyes were cleaved by irradiation with UV light having a wavelength of 365 nm for four minutes at 0.7 W/cm$^2$. Thereafter, the inside of the flow cell was washed with a buffer. The aforementioned elongation reaction, florescence detection, cleaving of the florescent dyes were repeated and a base sequence of the nucleic acid was determined.

Example 3

Instead of (2) Emulsion PCR and (3) Fixing beads having DNA on a surface thereof to the flow cell for nucleic acid analysis of Example 1, a method of preparing a template as disclosed in PTL 1 was used. The sequence reaction was performed with colonies formed on the substrate.

(1) Library Preparation
Performed as in Example 1.

(2) Coating the Flow Passage in the Flow Cell for Nucleic Acid Analysis with Acrylamide A 2% aqueous solution of acrylamide of 10 ml was mixed with a DMF solution of 165 µl where 100 mg/ml BRAPA had been dissolved therein, TEMED of 11.5 µl, and 50 mg/ml potassium persulfate of 100 µl. The mixed solution was then injected into the flow passage. The flow cell for nucleic acid analysis was maintained at a room temperature for one hour and 30 minutes and thereafter the flow passage was washed with water.

(3) Grafting the Primer on Acrylamide

An aqueous solution containing 0.5 µM forward primer and 0.5 µM reverse primer was fed inside the flow passage at a flow rate of 60 µl/sec for 75 seconds. The flow cell for nucleic acid analysis was then maintained at 50° C. for one hour. Thereafter, the inside of the flow passage was washed with a 5×SSC buffer.

(4) Colony Formation in the Flow Cell for Nucleic Acid Analysis (5) The library having been obtained in the library preparation was injected into the flow cell for nucleic acid analysis, where an amplification reaction was carried out to allow colonies to be formed.

(6) Nucleic Acid Analysis

According to the method of Example 1, a base sequence of the nucleic acid was determined.

Example 4

The aqueous solution of sodium azide in Example 1 was added with micro-glass beads (product name: EMB-10, a product by Potters-Ballotini Co., Ltd.). An average particle diameter of the micro-glass bead was 5 μm. The micro-glass beads were capable of reflecting, in an irregular manner, UV light that enters inside the flow passage, thereby further enhancing an efficiency of cleaving the florescent dyes.

INDUSTRIAL APPLICABILITY

A flow cell for nucleic acid analysis or a nucleic acid analyzer according to the present invention allows for performing a variety of nucleic acid reactions and nucleic acid analysis such as DNA sequencing.

REFERENCE SIGNS LIST 101, 201, 301, 401, 501, 601, 701(a), 701(b), 701(c), 801 first substrate
102, 202, 302, 402, 502, 602, 702(a), 702(b), 702(c), 802 optical filter
103, 203, 303, 403, 503, 603 hollow sheet
104, 204, 304, 404, 504, 604, 704(a), 704(b), 704(c), 804 hollow portion (or flow passage)
105, 205, 305, 405, 505, 605, 705(a), 705(b), 705(c) second substrate
106, 206, 306, 406 inlet
107, 207, 307, 407 outlet
408, 508, 608 near-ultraviolet ray cut filter
609 antireflection film
720 grooved sheet
821 protective film-attached sheet
822 protective film
910 flow cell for nucleic acid analysis
911 holder unit
912 stage unit
913 reagent container
914 liquid feeding unit
915 nozzle
916 nozzle transfer unit
917 detection unit
918 waste liquid container
919 light source
1020 first light
1021 second light
1022 third light
1023 bead carrier
1024 fourth light

The invention claimed is:

1. A flow cell for nucleic acid analysis, comprising:
a first substrate provided with an optical filter which reflects a first light for carrying out a photo-cleaving reaction with a nucleotide having an intramolecular fluorescent molecule via a photocleavable linker;
a hollow sheet having one or more hollow portions; and
a second substrate which transmits the first light,
wherein the first substrate, the hollow sheet, and the second substrate are attached to each other, with the hollow sheet being positioned between the first substrate, which underlies the hollow sheet, and the second substrate which overlies the hollow sheet, wherein the one or more hollow portions of the hollow sheet are enclosed by the optical filter of the underlying first substrate, the hollow sheet, and the overlying second substrate and form one or more flow passages;
one or more inlet and outlet holes on one of the first substrate and the second substrate and in fluid communication with the one or more flow passages;
a plurality of bead carriers, a surface of each of which bead carriers carries a plurality of molecules of the nucleotide having the intramolecular fluorescent molecule via the photocleavable linker, fixed inside the one or more flow passages, and
wherein the optical filter transmits a second light for exciting the fluorescent molecule and transmits a third light emitted from the fluorescent molecule.

2. The flow cell for nucleic acid analysis according to claim 1, wherein the optical filter is patterned such that the optical filter is in contact with the one or more flow passages.

3. The flow cell for nucleic acid analysis according to claim 1, wherein the second substrate comprises a near-ultraviolet ray cut filter transmitting the first light while reflecting a fourth light having a wavelength shorter than that of the first light.

4. The flow cell for nucleic acid analysis according to claim 1, wherein the second substrate comprises an antireflection film preventing reflection of the first light and the second light.

5. The flow cell for nucleic acid analysis according to claim 1, wherein a wavelength of the first light is 450 nm or less.

6. The flow cell for nucleic acid analysis according to claim 1, wherein a wavelength of the first light is 320 nm or more.

7. The flow cell for nucleic acid analysis according to claim 1, wherein a wavelength of the second light is 450 nm or more.

8. The flow cell for nucleic acid analysis according to claim 1, wherein a wavelength of the third light is 480 nm or more.

9. A flow cell for nucleic acid analysis, comprising:
a first substrate and a second substrate attached to each other,
a plurality of hollow passage grooves in the first substrate and forming flow passages, and
an optical filter on the first substrate, which optical filter reflects a first light for carrying out a photo-cleaving reaction with a nucleotide having an intramolecular fluorescent molecule via a photocleavable linker, on a bottom surface of the flow passages formed by the passage grooves, and the second substrate transmits the first light;
a plurality of bead carriers, a surface of which carries a plurality of molecules of the nucleotide having the intramolecular fluorescent molecule via the photocleavable linker, fixed inside the flow passages formed by the passage grooves,
wherein the optical filter transmits a second light for exciting the fluorescent molecule and transmits a third light emitted from the fluorescent molecule, and
wherein the passage grooves are enclosed by the optical filter of the attached first substrate and second substrate.

10. A flow cell for nucleic acid analysis, comprising:
a first substrate and a second substrate attached to each other,
a plurality of hollow passage grooves in the second substrate and forming flow passages, a surface of the first substrate opposite to the passage grooves being provided with an optical filter, which optical filter reflects a first light for carrying out a photo-cleaving reaction with a nucleotide having an intramolecular fluorescent molecule via a photocleavable linker, and the second substrate transmits the first light;
a plurality of bead carriers, a surface of each of which bead carriers carries a plurality of molecules of the nucleotide having the intramolecular fluorescent molecule via the photocleavable linker, are fixed inside the flow passages formed by the passage grooves, wherein the optical filter transmits a second light for exciting the fluorescent molecule and transmits a third light emitted from the fluorescent molecule, and wherein the passage grooves are enclosed by the attached first substrate and the second substrate.

11. A flow cell for nucleic acid analysis, comprising:

a first substrate and a second substrate attached to each other;

a sheet disposed between the first and second substrates, a plurality of hollow passage grooves in the sheet and forming flow passages, a bottom surface of the passage grooves on a side of the first substrate being defined by an optical filter, which optical filter reflects a first light for carrying out a photo-cleaving reaction with a nucleotide having an intramolecular fluorescent molecule via a photocleavable linker, and wherein the second substrate transmits the first light;

a plurality of bead carriers, a surface of each of which bead carriers carries a plurality of molecules of the nucleotide having the intramolecular fluorescent molecule via the photocleavable linker, fixed inside the flow passage, wherein the optical filter transmits a second light for exciting the fluorescent molecule and transmits a third light irradiated from the fluorescent molecule, and wherein the flow passages formed by passage grooves are enclosed by the attached first substrate and the second substrate.

12. A nucleic acid analyzer for analyzing nucleic acid, the analyzer comprising:

a flow cell for nucleic acid analysis including:

a first substrate provided with an optical filter which reflects a first light for carrying out a photo-cleaving reaction with a nucleotide having an intramolecular fluorescent molecule via a photocleavable linker;

a hollow sheet having one or more hollow portions;

a second substrate which transmits the first light, the first substrate, the hollow sheet, and the second substrate are attached to each other with the hollow sheet being positioned between the first substrate, which underlies the hollow sheet, and the second substrate, which overlies the hollow sheet, wherein the one or more hollow spaces, which are enclosed by the optical filter of the underlying first substrate, the hollow sheet, and the overlying second substrate form one or more flow passages, wherein the optical filter transmits a second light for exciting the fluorescent molecule and transmits a third light irradiated from a fluorescent molecule;

a holder unit configured to hold the flow cell for nucleic acid analysis and including;

a light source configured to irradiate the flow cell for nucleic acid analysis with the first light for changing a structure of the substance in the one or more flow passages;

a detection unit configured to irradiate the flow cell with a second light, and observe the third light from the fluorescent molecule corresponding to a sample in the flow cell, and wherein a plurality of bead carriers, a surface of each of which bead carriers carries a plurality of molecules of the nucleotide having the intramolecular fluorescent molecule via the photocleavable linker, are fixed inside the one or more flow passages.

* * * * *